United States Patent [19]
Tomlin

[11] Patent Number: 5,178,022
[45] Date of Patent: Jan. 12, 1993

[54] INERTIAL FILTRATION EXTERNAL DILUTION PROBE

[76] Inventor: Robert L. Tomlin, Rte. 3, Box 127, Waldron, Ark. 72958

[21] Appl. No.: 755,502

[22] Filed: Aug. 27, 1991

[51] Int. Cl.⁵ ............................................. G01N 1/24
[52] U.S. Cl. ................................................. 73/864.81
[58] Field of Search ........... 73/863.11, 863.23, 863.81, 73/863.83, 864.73, 864.81, 23.31–23.33

[56] References Cited

U.S. PATENT DOCUMENTS

| | | | |
|---|---|---|---|
| 2,814,952 | 12/1957 | Ryant, Jr. et al. | 73/863.83 |
| 3,960,500 | 6/1976 | Ross et al. | 73/863.11 |
| 4,094,187 | 6/1978 | Navarre, Jr. | 73/1 G |
| 4,101,282 | 7/1978 | Ririe | 73/863.11 |
| 4,379,412 | 4/1983 | Wood | 73/864.73 |
| 4,578,986 | 4/1986 | Navarre | 73/863.83 |
| 4,974,453 | 12/1990 | Hohorst | 73/863.11 |
| 4,974,455 | 12/1990 | McGowan et al. | 73/863.81 |

*Primary Examiner*—Robert Raevis
*Attorney, Agent, or Firm*—Dennison, Meserole, Pollack & Scheiner

[57] ABSTRACT

An inertial filtration dilution probe for sampling stack gas for analysis. The probe is based on a body having a central chamber passing from a first end of the body to a second end. One end of the central chamber is connected to a sampling tube to be inserted into a stack and the opposite end of the body has a port which is adapted to be selectively connected to a source of calibration gas or blowback gas. A filter divides the central chamber into an inlet portion and an outlet portion, with the sampling tube and port connected to the inlet portion. The probe further comprises a dilution eductor joined to the body, for mixing filtered stack gas with dilution gas and comprising an inlet for dilution gas, an outlet for diluted gas and a vacuum cavity therebetween. A sample passage within the body connects the outlet portion of the chamber to the vacuum cavity and a heating means encloses the body and eductor. The probe allows more accurate calibration of the gas analysis, since the calibration gas follows in the same path as the stack gas.

13 Claims, 3 Drawing Sheets

INERTIAL FILTRATION EXTERNAL DILUTION PROBE

BACKGROUND OF THE INVENTION

1. Field of the Invention

This invention relates to an apparatus for measuring the gaseous content of industrial process gas streams, in a process in which a portion of the gas stream is extracted, conditioned for analysis and transported to a gas analysis device.

2. Description of Related Art

Due to more stringent Government regulations requiring that continuous emission monitoring systems demonstrate up-times approaching 100% in some cases, and the trend to require ever smaller operations to continuously monitor their gaseous emissions, a clear need exists for a highly reliable sampling and analysis system that will not cause an unreasonable financial burden on the smaller regulated operations.

Many gas analysis systems are not specific to one gas, so that gases other than the gas or gases of interest may cause an erroneous response in the analysis system. Dilution of the process gas stream with air to achieve lower concentrations of the interfering gas has been demonstrated as a reliable way to eliminate many interference problems.

One of the difficulties encountered in the certification process for continuous emissions monitoring systems is to obtain agreement between the system being certified and an independent reference monitoring system. Reference methods suggest frequent installation of clean gas filters, i.e., between 3 hour sample runs, to insure accurate results. However, it has been required by regulation that a continuous emission monitoring system operate for an extended period of time of at least 168 hours without unscheduled maintenance and provide accurate readings throughout the extended period. A continuous emission monitoring system can overcome this handicap by frequent calibration, injecting a known calibration gas through the same sample flow path as the process gas being measured, and correcting, either automatically or manually, for any gas loss across the sample filters and other sampling system components. However, no dilution probe currently used in the art allows for calibration through all of the filters in the sample flow path, and thus cannot account for the condition of the filters. The existing systems utilize a coarse or primary stack gas filter and a second or fine filter, and while these systems calibrate through the second filter, they do not calibrate through the coarse or primary filter.

A typical dilution probe 10 is shown in FIG. 1. All of the system components are contained inside a stainless steel pipe 12 which is inserted through stack wall 14 into the process environment. The dilution probe includes a coarse filter 16, a restrictor plate 18, a fine filter 20, a glass orifice 22, and an eductor assembly 24, all subject to process temperature extremes between 35° and 580° F. The apparatus operates with dilution air entering through port 26 producing a diluted gas stream 28 exiting the apparatus through port 30. Calibration gas enters the apparatus through port 32.

The flow stability of the critical components and the ultimate dilution ratio stability are extremely difficult to control under widely changing process conditions. Attempts have been made to control the temperature of the probe body to reduce the effects of changing process temperatures, but have met with limited success due to the wide range of possible temperatures in the highly corrosive environments of the process streams.

A further problem with the existing technology is the inability to calibrate through the first or coarse filter 16. Although this filter consists only of a stainless steel screen, in most cases substantial loss may be caused by this filter if the filter is allowed to become wet or partially plugged with a reactive particulate from the process.

This dilution probe is calibrated with calibration gas entering through port 32, and being pulled through the fine filter 20 into glass orifice 22, and then through dilution eductor 24. Restriction plate 18 is required to prevent the calibration gas from simply passing into the process stream; instead, the process gas flow is blocked and 100% calibration gas is provided to the inlet of the fine filter during calibration. However, any losses associated with filter screen 9 are not compensated during calibration, and while adequate for some of the cleaner processes, this technique is not acceptable for applications that have lower process temperatures or high moisture conditions usually associated with wet scrubbing pollution control systems.

Due to the configuration utilized in the existing dilution probe systems, blowback of the coarse filter element is also a problem. To clean the filter screen requires a rather explosive air burst, and given the restriction inherent in the present design, attempts to blowback the coarse filter have been difficult to accomplish.

Placement of the dilution eductor filtering system inside the stack is highly undesirable, since most processes attempt to operate above the acid dew point, i.e., above 300° F., and many processes operate at temperatures between 280° F. and 1200° F. The prior art dilution probe shown in FIG. 1 cannot be used at temperatures above 580° F. Extracting a four to eight foot stainless steel tube that weighs as much as 25 pounds from a process duct at a temperature of 580° F. is not an east or safe maintenance procedure. Maintenance cannot be performed on the sampling system until the assembly nears ambient temperature and this may take several hours. Continuous emission monitoring systems that are required to obtain greater than 95% up-time could exceed the allowable down time requirements if any maintenance to the sampling system is required.

A dilution probe to be located primarily outside the stack is disclosed in U.S. Pat. No. 4,974,455. This probe includes a filter and associated heater located adjacent to the gas entrance port and an eductor and associated heater located adjacent to the sample exit port. The heaters are necessary to maintain the gas above its dew point as it passes through the apparatus. However, calibration of this apparatus is accomplished much in the same manner as in the previous apparatus, with a calibration gas introduced under pressure into the housing, forcing gas out through the coarse filter and back into the stack. In this process, the entire housing is purged of sample gas. Like the previous apparatus, this apparatus does not allow calibration through the coarse filter so that any gas lost through the coarse filter would not be measured.

SUMMARY OF THE INVENTION

It is therefore an object of the invention to provide a dilution probe to be located primarily outside the gas stack.

It is another object of the invention to provide a dilution probe in which calibration gas follows the same flow path as stack gas in order to more accurately calibrate the analysis system.

It is another object of the invention to provide a dilution probe in which the coarse filter may be easily and properly cleaned by blowback into the stack.

It is another object of the invention to provide a gas sampling and analysis system that allows accurate and interference free measurement of process gas streams while satisfying all requirements of the Environmental Protection Agency.

It is a further object of the invention to provide a process gas sampling and analysis system which provides a diluted gas sample to a gas analysis device and greatly simplifies the sampling system maintenance procedures while achieving a higher level of system performance with regard to dilution ratio precision and long term system drift.

These and other objects of the invention may be achieved through a inertial filtration dilution probe comprising a body having a central chamber passing from a first end of the body to a second end and a sampling tube having one end connected to the central chamber through its first end and having an opposite end adapted to be inserted into a process stack. The second end of the body has a port which is adapted to be selectively connected to a source of calibration gas or blowback gas.

A filter is located in the central chamber and divides the central chamber into an inlet portion and an outlet portion, with the sampling tube and the port for gas connected to the inlet portion.

The probe also includes a dilution eductor for mixing filtered stack gas with dilution gas and which comprises an inlet for the dilution gas, an outlet for diluted gas and a vacuum cavity therebetween. A sample passage connects the outlet portion of the central chamber to the vacuum cavity and includes a restriction orifice.

Finally, the probe comprises heating means enclosing both the body and the eductor.

By placing the critical components of the probe outside the stack environment, a wider range of process temperatures mat be tolerated, and the body, filter, and eductor mat be fabricated of lower temperature and highly inert materials such as fluoropolymers, polysulfones and polyamide-imides. Using these materials greatly reduces the possibility of unwanted gas reactions with sampling system components and provides much greater accuracy and stability in difficult or extremely corrosive applications.

Moreover, the filter element, critical orifice and eductor may be serviced without removing the probe from the stack, and probe maintenance may therefore be accomplished in minutes instead of hours. In fact, the probe may be cleaned in place, if necessary, by passing a rod of suitable size through the probe into the process stack.

Utilization of the probe therefore allows a process for extracting a gas sample for analysis from a process stream including the steps of extracting a gas sample from the stream without a primary filter at the probe tip, filtering the gas sample through a heated filter, drawing a predetermined quantity of filtered gas using a precision non-metallic dilution eductor that provides sample transport and dilution within a close coupled assembly and precisely controlled temperature, and passing the diluted sample to an analysis device.

The dilution probe of the invention has been developed to provide a lower cost, highly reliable alternative to existing sampling systems. The probe extracts a very small sample of the process stream, with a flow rate less than 1 liter per minute, and preferably 50 to 300 ml per minute. Due to the low flow rate, no filters are required in the sampling probe, with a large fraction of the particulate matter in the process gas settling out on the probe walls and being easily removed by blowback with air or steam. The sampling probe is typically a section of pipe approximately 0.670 inches outer diameter and 0.50 inches inner diameter, and formed of a material selected for compatibility with a process stream. Suggested materials for the probe include 316 stainless steel, Hastelloy C-276, Hastelloy C-276 with a Teflon liner, ceramic or rigid Teflon pipe. However, any material that is found compatible and non-reactive with the process stream may be used.

Response time requirements have been met with the probe of the invention by diluting the extracted gas from the probe immediately after passing through the heated filter. The low flow rate from the probe can be diluted with a wide range of air flows to meet response time and sensitivity requirements of a remote or local analysis system. Typical flow rates to an external analysis system are in the range of 5 to 15 liters per minute and give analytical instrument response time of 5 seconds to 3 minutes, depending upon the application. This response is adequate for most process control and environmental monitoring requirements.

Dilution of the process stream immediately at the sample source, with dry instrument air ($-40°$ F. dew point), allows a further simplification of the gas conditioning system. Permeation dryers, heated sample lines, gas heat exchangers and mechanical sample pumps are not required. Moreover, the dew point of the gas stream leaving the probe is largely a function of the dew point of the dilution air, due to the high dilution ratio of process gas to dilution air. Dilution ratios of 16:1 to 300:1 are easily achieved, and yield exit sample dew points at $0°$ to $-35°$ F., allowing use of unheated sample lines in all but the most extreme of environments. Dilution ratios of 10,000:1 or greater may also be accomplished with additional eductor stages.

The stack sample is pulled from the process stack using a precision low flow eductor. This eductor is driven by instrument quality air, and the same air that drives the eductor also dilutes the stack gas that is pulled in. The eductor assembly is incorporated into the body of the probe, with a precision orifice positioned at the inlet port to the eductor. An orifice protection filter may also be incorporated into the sample line between the filter and the eductor to protect the orifice during maintenance operations.

The diluted stack sample gas at the exhaust port of the eductor is allowed to pass through a sample manifold to a vent. A sample transport system, either local or remote, may then be used to extract diluted sample gas from the sample manifold for transport to the gas analysis system.

The probe of the invention may be utilized in connection with a local gas analysis system, in which case the probe and the gas analyzer would be located in a single enclosure, possibly 30 inches high by 24 inches wide by 8 inches deep.

The probe may also be used in conjunction with a remote analyzer, in which case the probe enclosure will be smaller, such as 20 inches high by 16 inches wide by 8 inches deep. In either case, a fiberglass or stainless steel enclosure is usually used but any construction found to be suitable for the ambient conditions at the sampling point is acceptable.

The probe generally uses at least a 2.5 inch standard pipe flange for sampling, but the enclosure may also be fitted with a 4 inch or 6 inch flange to suit existing sampling ports.

DESCRIPTION OF THE PREFERRED EMBODIMENTS

Figure 1:
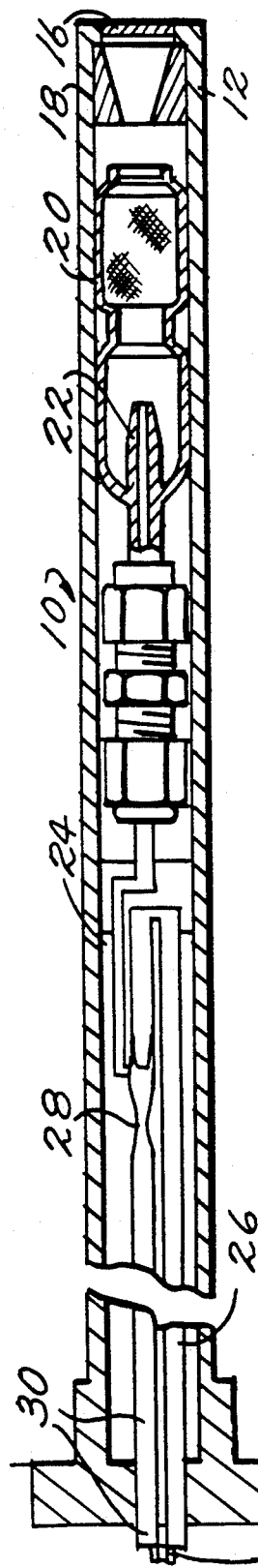
FIG. 1 is a longitudinal cross-section of a prior art dilution probe.
Figure 2:
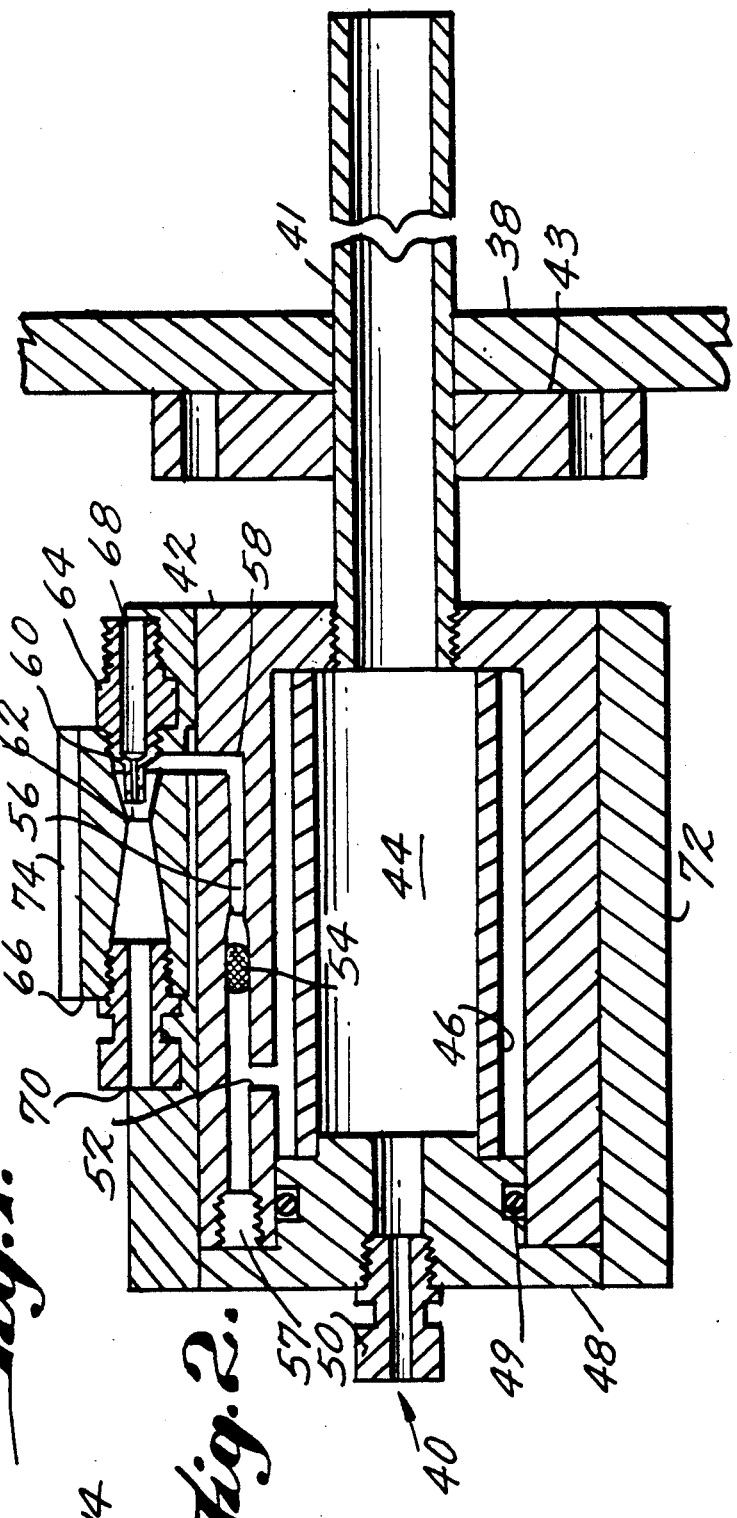
FIG. 2 is a longitudinal cross-section of a dilution probe according to the invention.

Shown in FIG. 2 is a probe 40 according to the invention inserted through a stack wall 38 to which it is secured by mounting flange 43. The probe includes a probe tip 41 inserted through the stack wall, the probe tip providing a path for the gas to a chamber 44 in probe body 42. Located in chamber 44 is a cylindrical filter 46, filter element 46 selected for its inertness to the process gas. This is usually a glass fiber element with Teflon binder having a filter rating of 0.1 μm. The opposite end of the body includes a filter cap 48 sealed with an O-ring 49. The filter element may be removed and replaced by removing filter cap 48.

Filter cap 48 includes a port 50 therein for introducing calibration and blowback gas. The body 42 is generally fabricated from Teflon to minimize sample loss due to unwarranted reactions of the process gas with the body.

On the opposite, downstream side of the filter there is a machined passage 52 having a filter 54 and critical orifice 56 located within. Filter 54 is a glass wool filter provided to protect the critical orifice assembly during maintenance to filter 46. While filter 54 normally does not require maintenance, the filter may be removed and replaced by removing screw closure 57 from machined passage 52.

The critical orifice assembly 56 may be fabricated from glass, sapphire or stainless steel. The current design uses a Lee Visco Jet orifice of stainless steel construction, consisting of a number of series/parallel jets that are contained in a housing 0.187 inches in diameter and between 0.66 and 0.72 inches of length, depending upon the desired restriction. The Lee Visco Jet allows for restriction with an orifice diameter as much as 25 times larger than a single hole orifice.

On the downstream side of the critical orifice there is a machined passage 58 passing into vacuum chamber 62 of eductor 60. The dilution eductor 60 is fabricated from Torlon 4203, a polyamide-imide high temperature resin with excellent resistance to chemical attack and excellent structural characteristics at elevated temperatures. Torlon thus offers the inertness of Teflon with the mechanical stability of metals.

The eductor 60 includes a jet 64 and body 66, all formed of Torlon. The vacuum generated by the eductor must be greater than 15 inches of mercury to assure a stable and accurate flow rate through vacuum chamber 62. The eductor also includes an input 68 for a source of dilution gas and an output 70 for diluted process gas.

The probe body including the eductor is inserted within an aluminum heater body 72 with extension 74 to enclose the eductor. The Teflon filter body 42 is pressed into the aluminum heater body 72, which regulates the temperature of the probe body to approximately 300° F.

Figure 3:
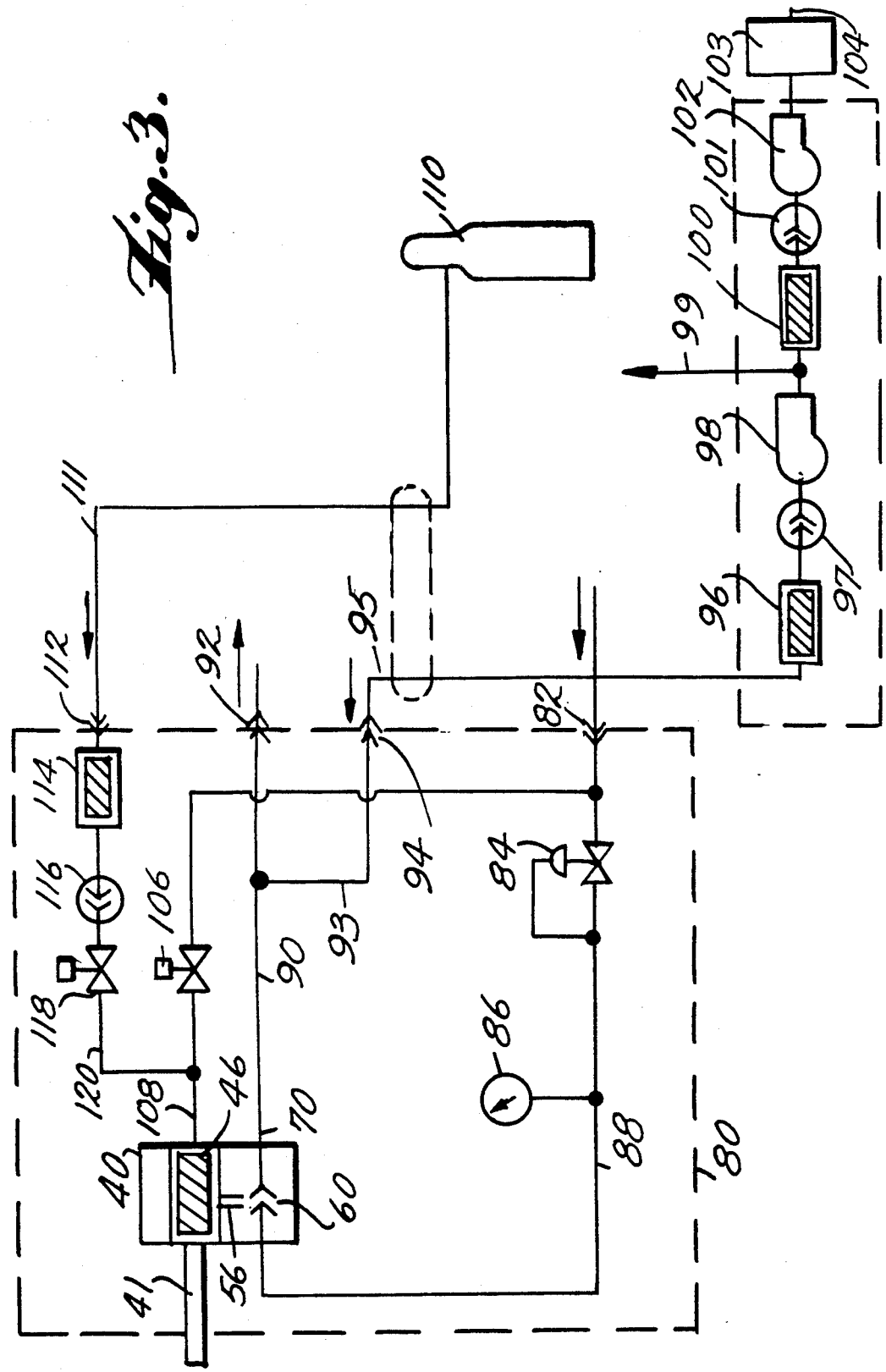
FIG. 3 is a schematic diagram of a sampling and analysis system with remote analyzer.

FIG. 3 shows the application of dilution probe 40 in conjunction with a gas analysis system with remote analyzer. The probe 40 is located in a heated enclosure 80, with enclosure temperature only roughly controlled to prevent freezing of enclosure components and provide increased stability. Process gas enters at the tip of probe 41, moving down the probe at a low flow rate of 10–300 ml per minute. Much of the large particulate drops out on the probe walls due to the low sample velocity. From probe 41, gas enters the analysis enclosure 80 and passes through the heated filter 46.

A regulated source of instrument air 82 is connected to the dilution/eductor jet 60 through an air pressure regulator 84 and a pressure gauge 86. The pressure regulator is a precision regulator that regulates the air pressure to within 0.03 PSI for a 10 PSIG change in input pressure. The air supply quality and pressure are important and the flow through eductor 60 not only creates the vacuum that moves the process gas through the probe system, but also is the dilution air used to dilute the process gas to lower concentrations. The process gas air flow rate is set and controlled by the critical orifice 56, while the air flow rate through eductor 60 may be set by varying the jet which is part of the eductor. Flow rates between 5 and 15 liters per minute may be selected in combination with different critical orifices 56, having flow rates between 50 and 300 ml per minute, to yield dilution ratios between 16:1 and 300:1. Dilution air, passing through line 88, and process gas meet in vacuum chamber 62 and the diluted process gas exits the eductor assembly through port 70. From the dilution eductor exhaust port, the diluted process gas passes through line 90 to a vent bulkhead 92 on the probe enclosure. A portion of the diluted sample is pulled through another line 93 and port 94 by sample transport pumps 98 and 102, through an unheated Teflon sample line 95, orifice protection filter 96 and orifice 97. A bypass vent 99 is provided after sample transport pump 98 in order to establish a reasonable transport time (usually less than 20 seconds) and may also be connected to a further analyzer. A portion of the flow is also passed through an orifice protection filter 100 and a flow control orifice 101 and is pumped to analyzer 103. Flow control orifice 101 is selected to obtain a desired flow rate to the remote analyzer 103. From the remote analyzer, diluted process gas flows to a vent manifold 104.

The probe is cleaned periodically by introducing high pressure blowback air from port 82 through blowback solenoid valve 106 and port 108 into the filter body and exiting into the process through probe 40. Solenoid valve 106 mat be operated either automatically or manually. The preferred method is to automatically energize solenoid valve 106 with either a local timer or remote controller. Blowback times may vary between 15 minutes for the most extreme applications and several hours for cleaner applications.

The probe assembly is calibrated by passing a gas of known concentration through all of the components in the sample analysis system that the process gas would flow through, and adjusting the response of the gas analysis system to equal the value of the known calibration gas. Calibrating in this manner allows for compensation of the total system for losses in filter elements and other pneumatic components, for changes in dilution air flow rates, and for changes in process gas flow rates.

A cylinder of calibration gas 110 is connected through line 111 to a bulkhead 112, which is connected to an orifice protection filter 114 and orifice 116 to a solenoid valve 118. Solenoid valve 118 allows the flow of calibration gas to be initiated either locally or remotely by a remote controller. The calibration valve is located as close to the filter port as possible to prevent condensation from forming in the calibration lines between calibrations. From solenoid valve 118, the calibration gas passes through calibration line 120 and line 108 into the filter cavity of the probe and passes through all system components at the same flow rates and conditions as the process gas.

Concerning the analysis device 103, the analyzer may be any one of several types normally used in the art including infrared, electrochemical, solid membrane or ion mobility. Among the gases which may be measured are one or more of $SO_2$, $Cl_2$, $ClO_2$, $NH_3$, HF, CO, $CO_2$, $O_2$, HCl, TRS, total sulfur, NO and $NO_2$.

Figure 4:
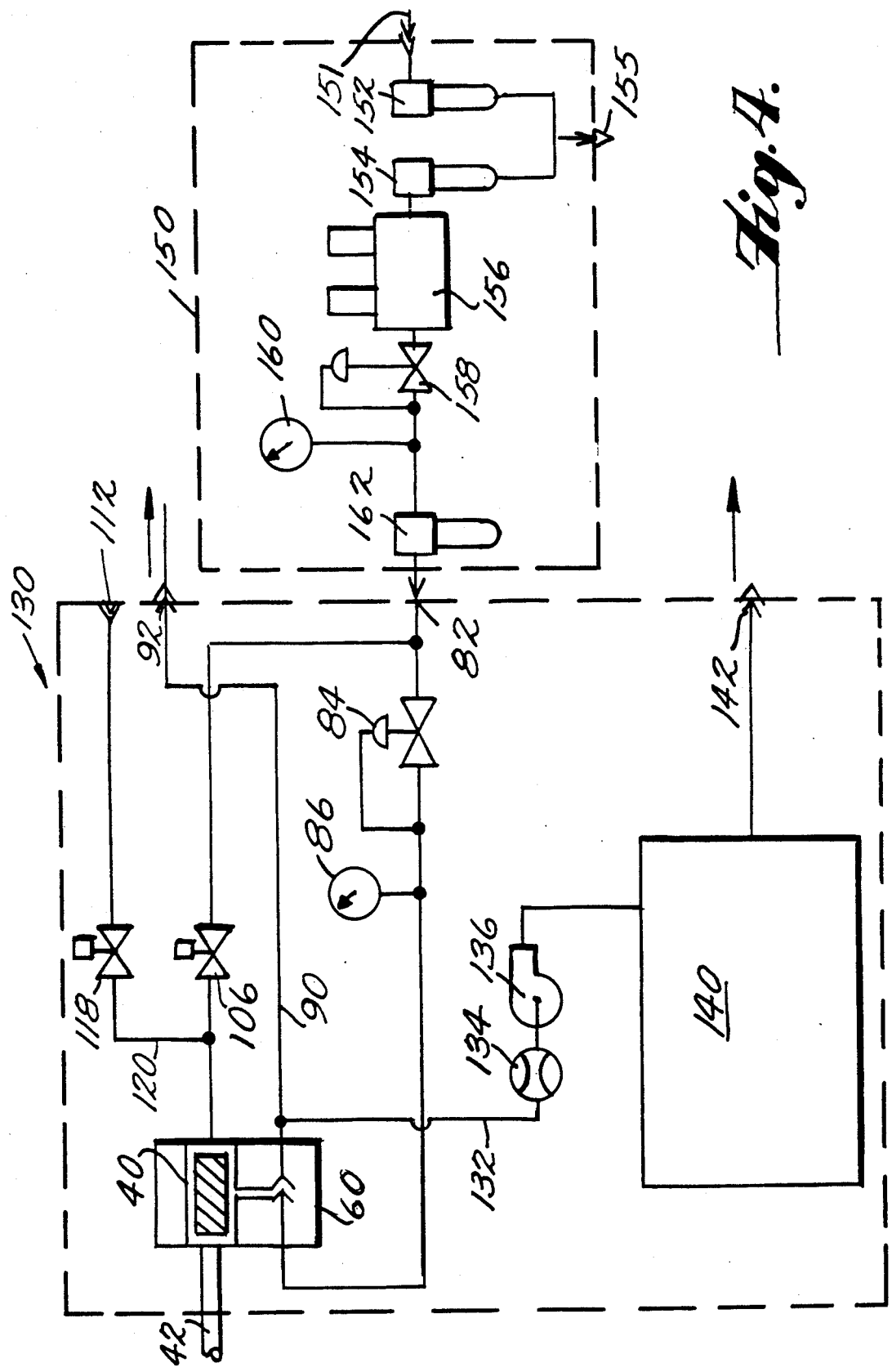
FIG. 4 is a schematic diagram of a sampling and analysis system with local analyzer.

Due to the compact size of the probe assembly, it is also possible to enclose the entire analysis unit in a single housing, and this embodiment is shown in FIG. 4. Housing 130 encloses all gas analysis elements, including an analyzer 140 of the type previously described. In addition, the gas analyzer used must be capable of withstanding temperatures of 120° to 150° F. and moderate vibration.

The analyzer elements shown in FIG. 4 generally correspond to those shown in FIG. 3, with the exception that a sample analysis line 132 is taken off diluted sample line 90. Gas analysis line 132 includes an orifice 134 and a pump includes a sample vent 142 Pump 136 may be replaced by an air aspirated eductor located between analyzer 140 and vent 142.

In addition, FIG. 4 shows a method of producing dry and conditioned air by utilizing an air clean-up unit 150 comprising, in series, a pair of filters 152 and 154 connected to a common drain 155, a regenerative air dryer 156, a pressure regulator 158, a gauge 160 and a final filter 162. This air clean-up unit is capable of removing trace quantities of gases to be analyzed from the air supply and can provide air with a dew point of at least −40° F.

What is claimed is:

1. A low-flow, inertial filtration dilution probe, comprising:
   a body with a central chamber passing from a first end of the body to a second end;
   a non-filtering sampling tube having one end connected to said central chamber through said first end of said body, and an opposite end adapted to be inserted into a process stack containing stack gas;
   a port in said second end of said body adapted to be selectively connected to a source of calibration gas or blowback gas;
   means for filtering stack gas dividing said central chamber into an inlet portion and an outlet portion, said sampling tube and said port connected directly to said inlet portion;
   an external plug in said second end of said body which is removable to expose said means for filtering and which is adapted for removal and servicing of said means for filtering;
   a dilution eductor joined to said body for mixing filtered stack gas with dilution gas and comprising an inlet for dilution gas, an outlet for removing diluted stack gas for analysis, and a vacuum cavity therebetween;
   a sample passage line within said body connecting said outlet portion to said vacuum cavity, and including a restriction orifice; and
   means for heating enclosing said body and said eductor,
   wherein a dilution eductor is located only downstream of said means for filtering.

2. A probe according to claim 1, additionally comprising second means for filtering located in said sample passage between said outlet portion and said restriction orifice.

3. The probe according to claim 2, additionally comprising a second external plug in said body which is removable to expose said second means for filtering and said restriction orifice, and which is adapted for removal of said second means for filtering.

4. A probe according to claim 1, wherein said port is located in said plug.

5. A probe according to claim 1, wherein said body, means for filtering and eductor are fabricated from an inert polymer.

6. A probe according to claim 5, wherein said polymer is selected from the group consisting of fluoropolymers, polysulfones and polyamide-imides.

7. A probe according to claim 1, wherein said sampling tube is formed of a material selected from the group consisting of stainless steel, Hastelloy, ceramic, Teflon and combinations thereof.

8. A probe according to claim 1, wherein said means for heating comprises an aluminum body.

9. A probe according to claim 1, wherein said means for filtering is cylindrical and said inlet portion is located in the center of said means for filtering.

10. A probe according to claim 1 wherein said sample passage is a machined passage.

11. A system for gas analysis comprising:
   a) an inertial filtration dilution probe according to claim 1;
   b) a housing enclosing said probe;
   c) a first external port on said housing connected to said outlet for diluted gas;
   d) a second external port on said housing connected to the port in said second end of said body;
   e) a third external port in said housing connected to said inlet for dilution gas through a pressure regulated valve and connected to said port and said second end of said body through a second valve.

12. A system according to claim 11, wherein said housing further comprises a gas analysis device connected to said outlet for diluted gas through a flow control valve and a means for transferring diluted gas to said analysis device.

13. A system according to claim 12, wherein said means for transferring comprises a pump or an eductor.

* * * * *